United States Patent
Abrams et al.

[11] Patent Number: 6,152,130
[45] Date of Patent: Nov. 28, 2000

[54] INHALATION DEVICE WITH ACOUSTIC CONTROL

[75] Inventors: Andrew L. Abrams, Westport, Conn.; Anand V. Gumaste, Robbinsville; Scott Fleming, Ewing, both of N.J.

[73] Assignee: Microdose Technologies, Inc., Monmouth Jct., N.J.

[21] Appl. No.: 09/097,106

[22] Filed: Jun. 12, 1998

[51] Int. Cl.[7] ............................................. A61M 16/00
[52] U.S. Cl. ................... 128/204.21; 128/203.12
[58] Field of Search .................. 128/204.21, 204.23, 128/204.26, 204.29, 203.24, 203.25, 200.16, 203.12, 204.28

[56] References Cited

U.S. PATENT DOCUMENTS

| | | | |
|---|---|---|---|
| 2,517,482 | 8/1950 | Hall | 128/206 |
| 3,507,277 | 4/1970 | Altounyan et al. | 128/208 |
| 3,518,992 | 7/1970 | Altounyan et al. | 128/208 |
| 3,635,219 | 1/1972 | Altounyan et al. | 128/266 |
| 3,795,244 | 3/1974 | Lax et al. | 128/266 |
| 3,807,400 | 4/1974 | Cocozza | 128/266 |
| 3,831,606 | 8/1974 | Damani et al. | 128/266 |
| 3,948,264 | 4/1976 | Wilke et al. | 128/266 |
| 3,957,965 | 5/1976 | Hartley et al. | 424/14 |
| 4,334,531 | 6/1982 | Reichl et al. | 128/200.14 |
| 4,349,531 | 9/1982 | Milodozeniec et al. | 424/27 |
| 4,776,990 | 10/1988 | Verity | 261/128 |
| 4,915,008 | 4/1990 | Sakashita | 84/735 |
| 5,069,107 | 12/1991 | Sakashita | 84/659 |
| 5,195,528 | 3/1993 | Hok | 128/716 |
| 5,267,555 | 12/1993 | Pajalich | 128/200.14 |
| 5,284,133 | 2/1994 | Burns et al. | 128/200.23 |
| 5,312,281 | 5/1994 | Talajasjo et al. | 446/25 |
| 5,331,953 | 7/1994 | Andersson et al. | 128/200.14 |
| 5,349,947 | 9/1994 | Newhouse et al. | 128/203.21 |
| 5,363,842 | 11/1994 | Mishelevich et al. | 128/200.14 |
| 5,369,977 | 12/1994 | Rhodes et al. | 73/23.3 |
| 5,372,128 | 12/1994 | Haber et al. | 128/203.21 |
| 5,383,469 | 1/1995 | Vreman et al. | 128/719 |
| 5,452,711 | 9/1995 | Gault | 128/200.14 |
| 5,458,135 | 10/1995 | Patton et al. | 128/200.14 |
| 5,459,280 | 10/1995 | Masuda et al. | 84/622 |
| 5,469,843 | 11/1995 | Hodson | 128/203.15 |
| 5,507,277 | 4/1996 | Rubsamen et al. | 128/204.23 |
| 5,522,383 | 6/1996 | Calvert et al. | 128/203.15 |
| 5,551,416 | 9/1996 | Stimpson et al. | 128/200.16 |
| 5,586,550 | 12/1996 | Ivir et al. | 128/200.16 |
| 5,655,523 | 8/1997 | Hodson et al. | 128/315 |
| 5,694,920 | 12/1997 | Abrams et al. | 128/200.16 |
| 5,699,649 | 12/1997 | Abrams et al. | 53/428 |
| 5,714,007 | 2/1998 | Pletcher et al. | 118/629 |
| 5,735,263 | 4/1998 | Rubsamen et al. | 128/200.14 |
| 5,758,637 | 6/1998 | Ivri et al. | 128/200.16 |
| 5,857,456 | 1/1999 | Sun et al. | 128/203.15 |
| 5,906,202 | 5/1999 | Schuster et al. | 128/203.23 |

FOREIGN PATENT DOCUMENTS

| | | | |
|---|---|---|---|
| 0174033 | 3/1986 | European Pat. Off. | A61M 15/00 |
| 9013327 | 11/1990 | European Pat. Off. | A61M 15/00 |
| 0506293 | 3/1992 | European Pat. Off. | A61M 15/00 |
| 2605249 | 10/1986 | France | B05B 1/02 |
| 2072536 | 10/1981 | United Kingdom | B05B 3/02 |
| 2262452 | 6/1993 | United Kingdom | A61M 15/00 |
| 9013328 | 11/1990 | WIPO | A61M 15/00 |
| 9419042 | 9/1994 | WIPO | A61M 15/02 |
| WO 97/26934 | 7/1997 | WIPO | A61M 15/00 |
| WO 98/20861 | 5/1998 | WIPO | A61K 9/28 |

*Primary Examiner*—Aaron J. Lewis
*Assistant Examiner*—Teena Mitchell
*Attorney, Agent, or Firm*—Hayes, Soloway, Hennessey, Grossman, & Hage, P.C.

[57] ABSTRACT

An fluid sensor to activate and control various components of an inhalation device. The fluid sensor includes an acoustic element, such as a microphone, positioned within said inhalation device to detect fluid within the device and output signals representative of the frequency and/or amplitude of the fluid. These signals control and activate an electrostatic plate and/or a high frequency vibrator.

14 Claims, 3 Drawing Sheets

INHALATION DEVICE WITH ACOUSTIC CONTROL

BACKGROUND OF THE INVENTION

1. Field of the Invention

The present invention relates generally to the field of inhalation devices, and more specifically, to inhalation devices that utilize acoustic control to facilitate breath activation of different systems of the inhalation device. Particular utility for the present invention is found in the area of facilitating inhalation of powdered medications.

2. Brief Description of Related Prior Art

Certain diseases of the respiratory tract are known to respond to treatment by the direct application of therapeutic agents. As these agents are most readily available in dry powdered form, their application is most conveniently accomplished by inhaling the powdered material through the nose or mouth. Alternatively, the drug in this form may be used for treatment of diseases other than those of the respiratory system. When the drug is deposited on the very large surface areas of the respiratory tract, it may be very rapidly absorbed into the blood stream; hence, this method of application may take the place of administration by injection, tablet, or other conventional means.

Several inhalation devices useful for dispensing this powder form of medicament are known in the prior art. For example, in U.S. Pat. Nos. 3,507,277; 3,518,992; 3,635,219; 3,795,244; and 3,807,400, inhalation devices are disclosed having means for piercing of a capsule containing a powdered medicament, which upon inhalation is drawn out of the pierced capsule and into the user's mouth and thus, into the user's lungs and respiratory system. Several of these patents disclose propeller means, which upon inhalation aid in dispensing the powder out of the capsule, so that it is not necessary to rely solely on the inhaled air to suction powder from the capsule. For example, in U.S. Pat. No. 2,517,482, issued to Hall, a device is disclosed having a powder containing capsule which is pierced by manual depression of a piercing pin by the user. U.S. Pat. No. 3,831,606 discloses an inhalation device having multiple piercing pins, propeller means, and a self-contained power source for operating the propeller means via external manual manipulation, so that upon inhalation the propeller means aids in dispensing the powder into the stream of inhaled air. See also U.S. Pat. No. 5,458,135.

These prior art devices present several problems and possesses several disadvantages which are remedied by the inhalation devices of the present invention. For instance, these prior art devices require that the user exert extreme effort in inhalation to effect dispensing or withdrawal of powder from a pierced capsule into the inhaled air stream.

The above description of the prior art is taken largely from U.S. Pat. No. 3,948,264 to Wilke et al, who disclose a device for facilitating inhalation of a powdered medication. A capsule piercing structure is provided, which upon rotation puts one or more holes in the capsule, which contains medication, so that upon vibration of the capsule by an electro-mechanical vibrator, the powdered drug may be released from the capsule. The electromechanical vibrator includes, at its innermost end, a vibrating plunger rod which is connected to a mechanical solenoid buzzer for energizing the rod to vibrate. The buzzer is powered by a high energy electric cell and is activated by an external button switch. Moreover, as noted above, in Wilke et al.'s disclosed device, vibration of the powder is activated by depressing a push button. This can be difficult and painful for some users (e.g., patients suffering from extreme arthritis). Finally, in order to use Wilke et al.'s disclosed inhaler most efficaciously, the user must depress the vibration-actuating push button at precisely the same time that the user begins inhalation. This can also be difficult for some users (e.g., very young patients, patients suffering from neuromuscular disorders, etc.).

The prior art, such as described above, is dominated by inhaler devices that are activated by some mechanical means of activation, e.g., airflow sensors that include: flapper valves, turbine valves, swirl generators, vortex measurement devices, hot wire, direct pressure drop, ultra sonic, Doppler shift measurement, etc.

SUMMARY OF THE INVENTION

Accordingly, the present invention solves the aforementioned drawbacks of related art devices by providing an air flow sensor for controlling various components of an inhalation device. Included in the preferred embodiment is an acoustic controller, the acoustic controller including an acoustic element to sense air flow around the element and for producing signals representative of a frequency and amplitude of the air flow, the signals being used to control (e.g., activate, deactivate, apply incremental voltage, etc.) certain components of the inhalation device.

Preferably, acoustic element is a microphone element or pressure transducer positioned within the air passage of an inhalation device, (e.g., a dry powder inhaler) that produces signals in response to the inhalation air flow, these signals are used to control certain components of the inhaler, e.g., a high frequency vibrator, an electrostatic plate, timer, counter, etc. Also preferably, these signals are used to activate/control certain components of the inhalation device to maximize the inhalation effectiveness to obtain maximum patient benefit from the medicament.

Thus, the present invention provides a fully automated inhalation device, that is breath activated, that permits optimal utilization of the particular medication. For example, acoustic signals can be used to trigger the high frequency vibrator and electrostatic plate only when the patient has achieved optimum (e.g., maximum) inhalation effort, thereby ensuring that the full (proper) dosage of medicament properly enters the patient's respiratory system. Alternatively, these signals (breath-activated signals) can be used to progressively apply increasing power to, or, sequentially activate/deactivate the various components of the inhalation device to achieve optimal inhalation dosage.

It will be appreciated by those skilled in the art that although the following Detailed Description will proceed with reference being made to preferred embodiments and methods of use, the present invention is not intended to be limited to these preferred embodiments and methods of use. Rather, the present invention is of broad scope and is intended to be limited as only set forth in the accompanying claims.

Other features and advantages of the present invention will become apparent as the following Detailed Description proceeds, and upon reference to the Drawings, wherein like numerals depict like parts, and wherein:

DETAILED DESCRIPTION OF PREFERRED EMBODIMENTS

Figure 1:
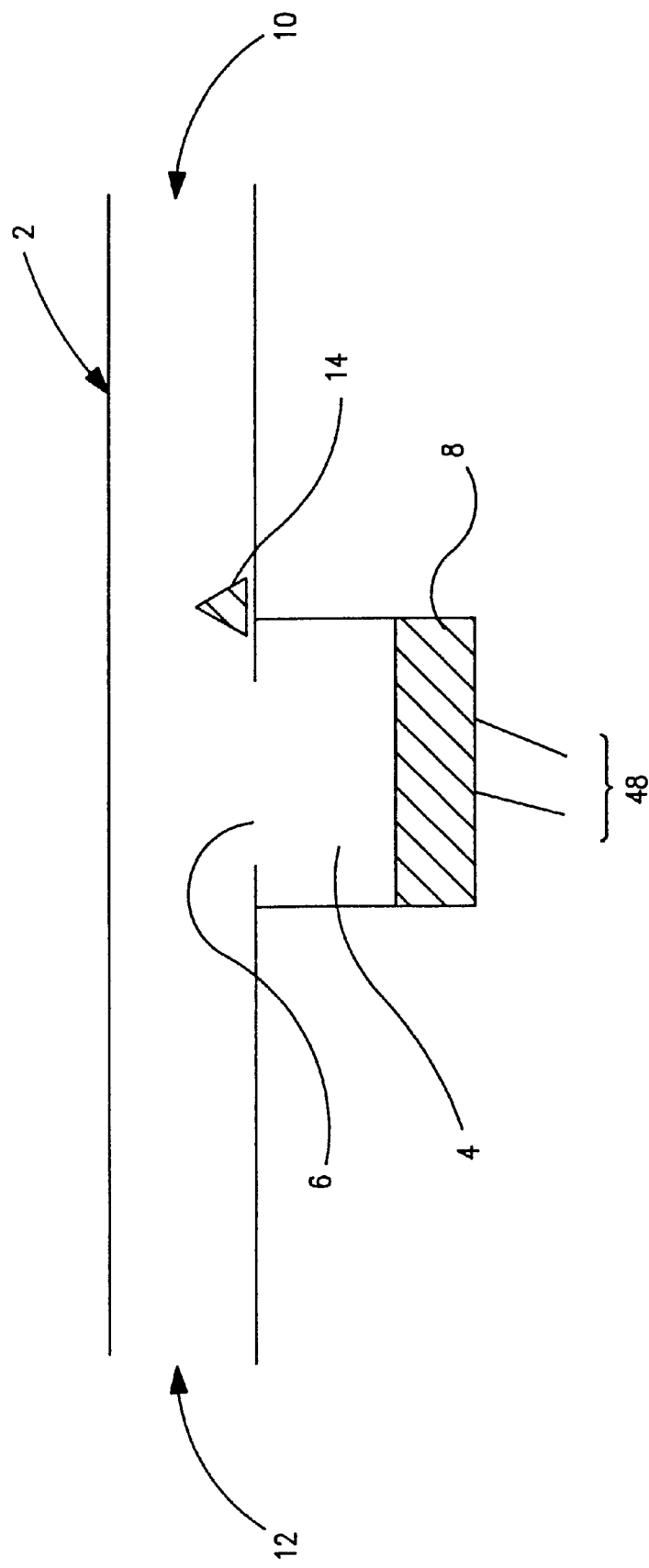
FIG. 1 is a cross-sectional view of a typical inhalation device and the acoustic controller of the present invention.
Figure 2:
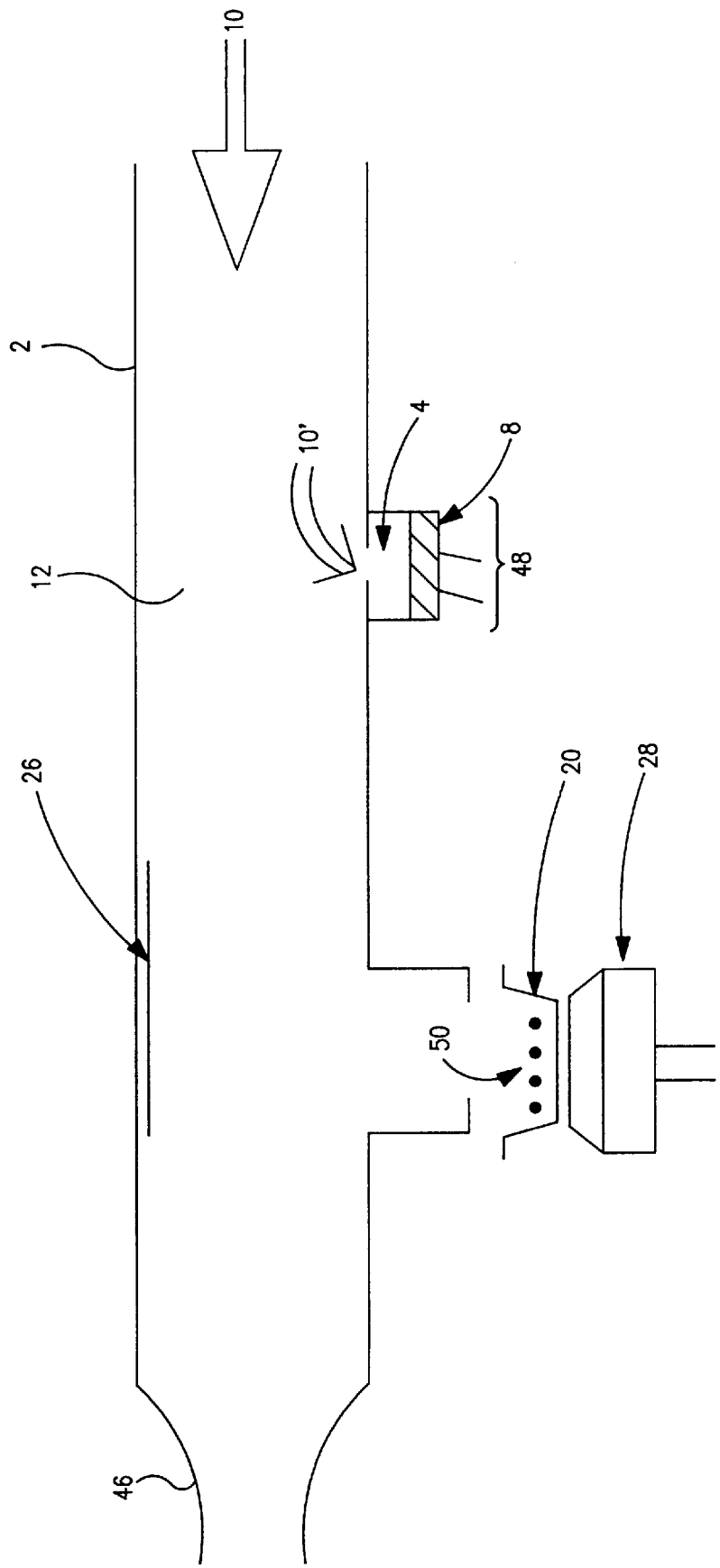
FIG. 2 is an expanded cross-sectional view of FIG. 1.

Referring to FIGS. 1 and 2, a cross-sectional view of an airflow passage 12 of an inhalation device 2 is depicted. It should be noted at the outset that the airflow passage 12 depicted in FIG. 1 is a generalized airflow passage of a typical inhalation device, such as those discussed above. However, the present invention is intended to be adapted to any inhalation device, regardless of the particular geometry of the airflow passage. At its most basic level, the present invention operates by providing an air flow sensor 8 to detect air flow turbulence around the sensor 8 (i.e., inspiratory air flow rate of a user of the inhaler) and to control various components of the inhalation device 2, as a function of the amplitude and/or frequency of the detected airflow turbulence, as described below.

As shown in FIG. 1, air 10 (or other fluid) enters the airflow passageway 12, typically by the respiratory activity of a patient inhaling on the device 2. As air 10 flows through the passage 12, a portion thereof flows through the opening 6 in the passage 2 into a cavity 4. Placed within the cavity 4 is an air flow sensing device 8. Preferably, the air flow sensing device 8 is an acoustic sensing device, e.g. a microphone. Also preferably, microphone 8 is adapted to produce appropriate signals 48 in response to the airflow detected within the cavity 4. The amplitude and frequency of the airflow within the cavity 4 is a function of the airflow rate 10 within the air passage 12 of the device 2. Thus, output signals 48 from the microphone 8 will vary in both frequency and amplitude as a function of air flow rate within the cavity (which is a function of flow rate within the passage 12), and thus, can be used to control various components of the inhaler 2 as a function of frequency and/or amplitude, as described below. Those skilled in the art will appreciate that the shape of the cavity 4 and the size of the opening 6 are chosen in accordance the particular geometry of the air passage 12, the air flow rate 10 through the passage 12, and/or the frequency response and/or sensitivity of the microphone 8; and all such variations are within the scope of the present invention. Preferably, as noted above, the shape of the cavity 4 and the size of the opening 6 are chosen to permit at least a portion of the air within the passage 2 to enter the cavity 4 with sufficient amplitude to induce a response from the microphone 8.

Referring now to FIG. 2, an expanded cross-sectional view of an embodiment of the air flow sensor (described with reference to FIG. 1, above) in a dry powder inhaler, such as disclosed in U.S. Pat. No. 5,694,920. Depicted in FIG. 2 are the components of a typically dry powder inhaler 2. A mouthpiece 46 is provided for a user (i.e., patient) to inhale on the device 2. A high-frequency vibratory mechanism 28 (e.g., piezoelectric element, ultrasonic acoustic transducer, or other electro/mechanical vibratory mechanism, etc.) is provided to vibrate a container 20 (e.g., blister capsule) of dry powdered medicament 50 to suspend particles of the medicament into the air passage 12. To further aid the suspension of particles, an electrostatic potential plate 26 can be provided to draw particles of a certain charge (i.e., a charge opposite to that of the electrostatic plate 26) into the air stream 10. In this embodiment, a portion 10' of the air 10 drawn into the air passage 12 is induced into the cavity 4, to be detected by the microphone element 8. Upon detection of airflow, the microphone element produces output signals 48 proportional in amplitude and frequency of the air flow rate within the air passage 12. The output signals 48 are used to control either the high-frequency vibrator 28 and/or the electrostatic plate 26, or other components of the inhaler, as described below.

Figure 3:
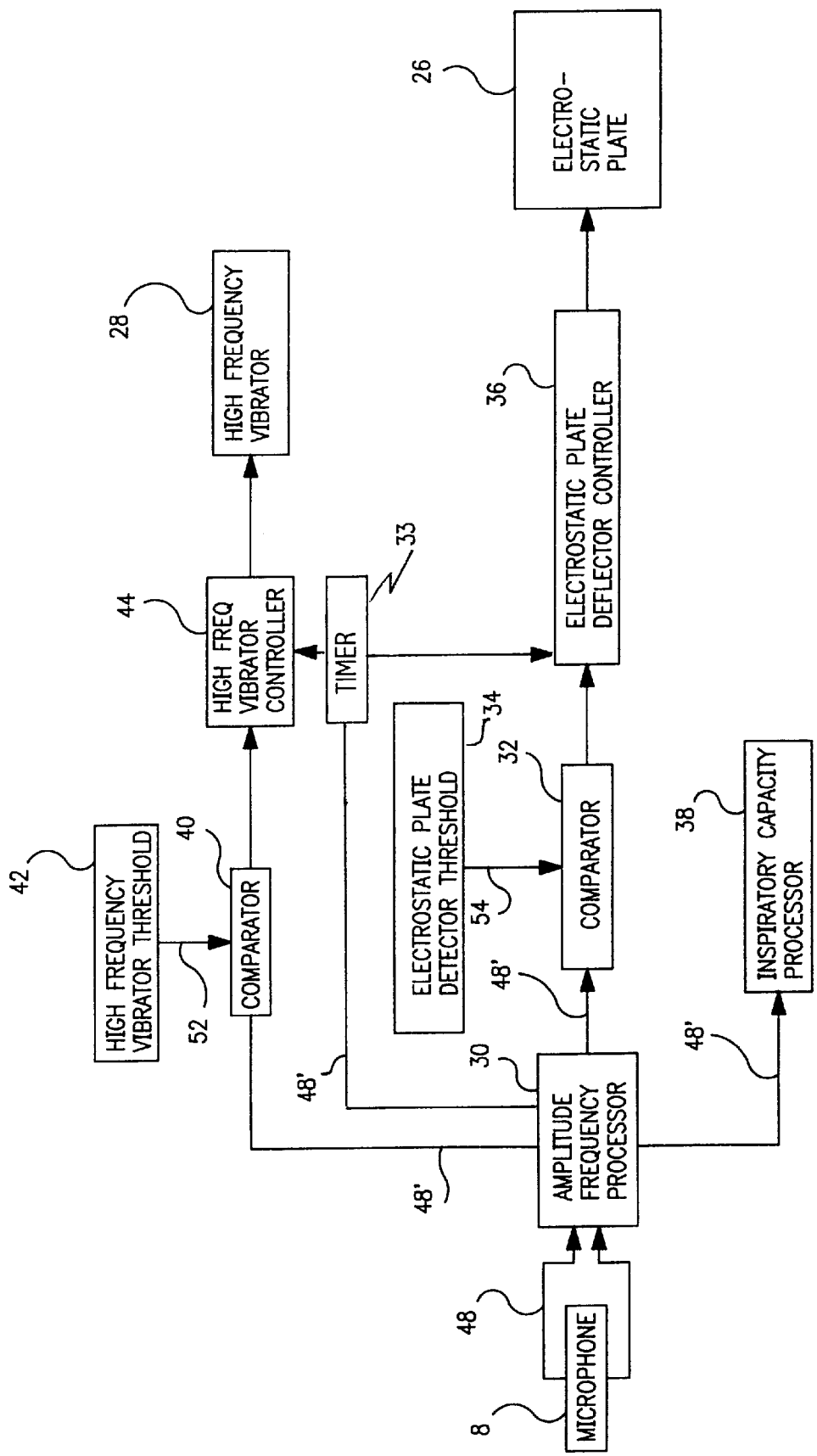
FIG. 3 is a functional block diagram of a preferred embodiment of the acoustic controller of the present invention.

FIG. 3 is a block diagram representation of the acoustic control system of the present invention for a dry powder inhaler. As described above, the microphone element 8 produces signals 48 in response to detected airflow 10'. These signals are processed by an amplitude/frequency processor 30 to condition the signals 48 and to determine the amplitude and/or frequency of the output signals 48. The amplitude/frequency processor produces output signals 48' to control the high-frequency vibrator and/or electrostatic plate. To that end, output signals 48' are input into a comparator circuit 40 and/or 32 and compared with a reference threshold signal 42 and/or 34, respectively.

It should be understood that signals 48 and 48' are indicative of the airflow rate 10, described above. The present invention is intended to be controllable as a function of frequency and/or amplitude of signals 48, thus, amplitude/frequency processor can be adapted to condition the signals 48 in terms of amplitude or frequency are both. High frequency vibrator threshold 42 produces a signal 52 which represents the minimum voltage and/or frequency required to activate the high frequency vibrator controller 44 (which, in turn, activates the high frequency vibrator 26). Comparator 40 compares signal 52 with signal 48' and if the signals have equal amplitude and/or frequency (within some predetermined error margin), comparator activates the high frequency vibrator controller 44, which activates and directly controls the high frequency vibrator 26. Similarly, electrostatic plate deflector controller 36 is activated by an equal match of signals 48' and 54 by the comparator 32. Electrostatic plate detector threshold 34 produces signal 54 which represents the minimum voltage and/or frequency required to activate the electrostatic plate 26.

Inspiratory capacity processor 38 is provided to compute the peak inspiratory flow 10 (represented by signals 48 and 48') of the patient. Although not shown in the drawings, this information can be used to adjust the threshold signals of the high frequency vibrator threshold 42 and/or electrostatic plate detector threshold 34. Of course, to accomplish this, the high frequency vibrator threshold 42 and/or electrostatic plate detector threshold 34 must be programmable, as is known in the art. In this way, the microphone 8 can be programmed to trigger the various components of the inhaler to adjust for varying inspiration flow rates from patient-to-patient or individually. Thus, for example, the inspirator control scheme of the present invention can be self-adjusting to account for a patient's decrease in inspiratory flow rate caused by, for example, decreased lung capacity. Alternatively, the processor 38 can be modified to sequentially turn on the various components herein described (e.g., vibrator, electrostatic plate, etc.) at optimal inhalation times (e.g., peak inhalation effort). Thus, for example, the processor 38 can be modified to activate the vibrator at a time just prior to the user's peak inhalation effort, then to activate the electrostatic plate subsequently, thereby inducing the medicament into the airstream at a time that produces optimal respiratory absorption of the medicament. Moreover, processor 38 can be adapted with appropriate memory to track a patient's inspiratory flow rate which can be used to adjust the powdered medicament 50 to achieve maximum medication benefit.

Thus, it is evident that there has been provided an inhalation device with acoustic control and method for operating same that fully satisfy both the aims and objectives hereinbefore set forth. It will be appreciated that although specific embodiments and methods of use have been presented, many modifications, alternatives and equivalents are possible. For example, processor 30, threshold signal generators 34 and 42, comparators 42 and 32 and can be any known digital (e.g., microprocessor) or analog circuitry and/or associated software to accomplish the functionality described herein. Although the various components described in FIG. 3 have been described in a modular fashion, those skilled in the art will recognize that each of these components can be discrete off-the-shelf or custom components, or can be included in a single, unified system.

The device of the present invention can be modified by permitting the microphone signals 48 and 48' to directly control activation of the high frequency vibrator 28 and/or electrostatic plate 26, thereby bypassing the comparators 40 and/or 32. In this way, microphone 8 can be adapted to activate these components in a binary fashion that is not dependent upon flow rate. Also, it will be understood to those skilled in the art that the thresholding circuits 42 and 34, the amplitude/frequency processor 30 and the inspiratory capacitor processor 38 can be adapted to permit user (patient) control and user-definable presets (i.e., minimum flow rate for activation, etc).

In addition, comparators 40 and 32 can be adapted to permit generation of activation signals based differing signal strengths and/or frequency. Thus, for example, the high frequency vibrator can be adapted to activate only when a signal frequency of 1 Khz is achieved, while the electrostatic plate will only activate when a signal strength of 35 mV. is obtained.

Other modifications are also possible. For example, the microphone 8 can be positioned directly on the inner wall of the airflow passage 12 of the device 2, instead of within the cavity 4. Also, as shown in FIG. 1, a turbulence generator 14 can be provided to generator air turbulence within the air passage 12. This modification, for example, can be used in an inhalation device that would otherwise not permit a portion 10' of the air 10 to enter the cavity 4. In addition, instead of a microphone 8, the acoustic element can be any known fluid pressure transducer (e.g., air pressure transducer) that will output appropriate signals as a function of fluid pressure (amplitude) and/or frequency. Accordingly, the present invention can be appropriately modified to operate in any fluid medium (other than air), to provide automatic acoustic control.

Still other modifications are possible. For example, although not shown in the drawings, the present invention can be provided with a timer that is controlled by signals 48'. The timer can be appropriately modified to control a schedule of when the device may be activated, to avoid, for example, an overdose. Thus, for example, the timer may be modified to only permit activation of the components of the device at certain times of the day. Moreover, the timer may be appropriately modified to permit downloading of data related to usage (e.g., time of day used, dosage of medicament, inhalation effort, etc.). This data can be particularly relevant for clinical trials where it is important to track the recommended dosage and times of medication. Of course, the previous description could be accomplished with a counter, or the like, that simply counts the amount of times that the device has been used.

Although the present invention has been directed to an acoustic control scheme for a dry powder inhaler 2, the present invention is not so limited. On the contrary, the present invention is intended to be adapted for any inhalation device that would require a control mechanism (such as described herein) based breath (inhalation) detection. For example, an anesthetic device could be modified with the breath sensor and controller as provided herein to monitor and control the amount of anesthetic a patient receives. Additionally, the acoustic sensing element can be used to measure peak inspiratory and/or expiratory flow of a particular patient, and record this information for downloading and analysis.

Although the preceding detailed description has provided several embodiments of controlling various components of an inhalation device using acoustic signals representative of the amplitude and/or frequency of inhalation, these have been provided only as examples of achieving an acoustic control scheme, and other alternatives will become apparent to those skilled art. Accordingly the present invention is intended to cover all such alternatives, modifications, and equivalents as may be included within the spirit and scope of the invention as defined only by the hereinafter appended claims.

What is claimed is:

1. An air inhalation device for delivering powdered medicament from a container, said container comprising: an acoustic controller, said acoustic controller including an acoustic microphone element configured to sense sound of air flow around said acoustic microphone element and to produce signals representative of said air flow, and a high frequency vibrator configured for vibrating said container in response to said signals, said vibrator thereby being operable for inducing said medicament into said air flow.

2. An inhalation device as claimed in claim 1, wherein said signals control activation/deactivation of an electrostatic plate to attract certain particles towards said electrostatic plate and into said air flow.

3. An inhalation device as claimed in claim 1, wherein said signals control activation of a timer, said timer being configured to control said vibrator.

4. An inhalation device as claimed in claim 1, wherein said device further comprises an inspiratory capacity processor configured to obtain data related to air flow rate around said acoustic microphone element and to control said vibrator using said data.

5. An inhalation device as claimed in claim 4, wherein said data includes a minimum and maximum air flow rate indicative of inspiratory and expiratory effort of a user of said inhalation device.

6. An inhalation device as claimed in claim 1, wherein said acoustic microphone element is optimally positioned within said inhalation device to obtain optimal air flow around said acoustic microphone element.

7. An inhalation device as claimed in claim 1, wherein said acoustic microphone element comprises an air pressure transducer.

8. An inhalation device comprising: an air flow passage; an acoustic controller including an acoustic microphone element positioned within said an air flow passage and being configured to sense sound of air flow around said acoustic microphone element and for producing signals representative of a frequency and amplitude of said air flow; a high frequency vibrator configured to vibrate a container of powdered medicament and induce said medicament into said air flow, said high frequency vibrator being controlled by said signals; and an electrostatic plate configured to attract certain particles of said powdered medicament towards said electrostatic plate and into said air flow, said electrostatic plate being controlled by said signals.

9. An inhalation device for delivering powdered medicament from a container, said device comprising:

an acoustic controller including an acoustic microphone element configured to sense sound of air flow around said acoustic microphone element and to produce signals representative of said air flow;

and an electrostatic plate configured for attracting certain particles of said medicament from said container and into said air flow in response to said signals.

10. An inhalation device as claimed in claim 9, wherein said signals control activation of a timer, said timer being configured to control said electrostatic plate.

11. An inhalation device as claimed in claim 9, wherein said device further comprises an inspiratory capacity processor configured to obtain data related to air flow rate around said acoustic microphone element and to control said electrostatic plate using said data.

12. An inhalation device as claimed in claim 9, wherein said data includes a minimum and maximum air flow rate indicative of inspiratory and expiratory effort of a user of said inhalation device.

13. An inhalation device as claimed in claim 9, wherein said acoustic microphone element is optimally positioned within said inhalation device to obtain optimal air flow around said acoustic microphone element.

14. An inhalation device as claimed in claim 9, wherein said acoustic microphone element comprises an air pressure transducer.

* * * * *

UNITED STATES PATENT AND TRADEMARK OFFICE
CERTIFICATE OF CORRECTION

PATENT NO. : 6,152,130
DATED : November 28, 2000
INVENTOR(S) : Abrams et al.

It is certified that error appears in the above-identified patent and that said Letters Patent is hereby corrected as shown below:

Column 6,
Line 21, "said container comprising" should be -- said device comprising --.

Signed and Sealed this

Fourth Day of January, 2005

JON W. DUDAS
*Director of the United States Patent and Trademark Office*